United States Patent
Holm et al.

(10) Patent No.: US 10,759,726 B2
(45) Date of Patent: Sep. 1, 2020

(54) PROCESS FOR THE PREPARATION OF ETHYLENE GLYCOL FROM SUGARS

(71) Applicant: HALDOR TOPSØE A/S, Kgs. Lyngby (DK)

(72) Inventors: Martin Spangsberg Holm, Copenhagen (DK); Christian Mårup Osmundsen, Gentofte (DK); Esben Taarning, Frederiksberg (DK); Amanda Birgitte Sølvhøj, Copenhagen (DK); Morten Boberg Larsen, Smørum (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 16/068,581

(22) PCT Filed: Jan. 5, 2017

(86) PCT No.: PCT/EP2017/050183
§ 371 (c)(1),
(2) Date: Jul. 6, 2018

(87) PCT Pub. No.: WO2017/118686
PCT Pub. Date: Jul. 13, 2017

(65) Prior Publication Data
US 2019/0010104 A1 Jan. 10, 2019

(30) Foreign Application Priority Data
Jan. 7, 2016 (DK) .................................. 2016 00008

(51) Int. Cl.
| *C07C 29/141* | (2006.01) |
| *C07C 29/145* | (2006.01) |
| *C07C 29/60* | (2006.01) |
| *C07C 27/04* | (2006.01) |

(52) U.S. Cl.
CPC ............ *C07C 29/141* (2013.01); *C07C 27/04* (2013.01); *C07C 29/145* (2013.01); *C07C 29/60* (2013.01); *Y02P 20/132* (2015.11); *Y02P 20/52* (2015.11)

(58) Field of Classification Search
CPC ..... C07C 29/141; C07C 29/145; C07C 29/60; C07C 27/04; Y02P 20/132; Y02P 20/52
See application file for complete search history.

(56) References Cited

U.S. PATENT DOCUMENTS

| 4,200,765 A | 4/1980 | Goetz |
| 4,317,946 A | 3/1982 | Costa |
| 4,321,414 A | 3/1982 | Costa |
| 4,496,781 A | 1/1985 | Jacobson et al. |
| 4,762,817 A | 8/1988 | Logsodon et al. |
| 5,096,931 A | 3/1992 | Wittenberg et al. |
| 5,210,337 A | 5/1993 | Broussard |
| 5,334,778 A * | 8/1994 | Haas ................ C07C 29/141 568/862 |
| 5,393,542 A | 2/1995 | Stradal et al. |
| 6,255,541 B1 | 7/2001 | Paatero et al. |
| 6,297,408 B1 | 10/2001 | Haas et al. |
| 6,297,409 B1 | 10/2001 | Choque et al. |
| 7,094,932 B2 | 8/2006 | Majerski et al. |
| 9,126,912 B1 | 9/2015 | Chen et al. |
| 2004/0022912 A1 | 2/2004 | Majerski et al. |
| 2007/0249871 A1 | 10/2007 | Almeida Lenero et al. |
| 2007/0287868 A1 | 12/2007 | Arredondo et al. |
| 2008/0045749 A1 | 2/2008 | Arredondo et al. |
| 2008/0228014 A1 | 9/2008 | Bloom |
| 2011/0021845 A1 | 1/2011 | Zim et al. |
| 2012/0172633 A1 | 7/2012 | Zhang et al. |
| 2013/0253230 A1 | 9/2013 | Norman et al. |
| 2014/0039224 A1 | 2/2014 | Adlaf et al. |
| 2015/0329449 A1* | 11/2015 | Schreck ................ B01J 21/02 568/863 |
| 2016/0177185 A1 | 6/2016 | Bauer |
| 2017/0009008 A1 | 1/2017 | Van Walsem |

FOREIGN PATENT DOCUMENTS

| CN | 1894188 A | 1/2007 |
| CN | 101925569 | 12/2010 |
| CN | 102190562 A | 9/2011 |
| CN | 102649081 A | 8/2012 |
| EP | 0 002 908 B1 | 7/1979 |
| JP | 360218341 | 11/1985 |
| RU | 2351581 C2 | 4/2009 |
| TW | 170739 B | 1/2002 |

(Continued)

OTHER PUBLICATIONS

Hawley's Condensed Chemical Dictionary (recycling, Mar. 2007, 1 page).*
International Search Report (PCT/ISA/210) dated Mar. 29, 2017, by the European Patent Office as the International Searching Authority for International Application No. PCT/EP2017/050183.
Written Opinion (PCT/ISA/237) dated Mar. 29, 2017, by the European Patent Office as the International Searching Authority for International Application No. PCT/EP2017/050183.
Danish Search Report dated Jul. 26, 2016.

(Continued)

*Primary Examiner* — Rosalynd A Keys

(74) *Attorney, Agent, or Firm* — Buchanan Ingersoll & Rooney P.C.

(57) ABSTRACT

A process for the preparation of ethylene glycol and other $C_1$-$C_3$ hydroxy compounds comprising the steps of hydrogenating a composition comprising $C_1$-$C_3$ oxygenate compounds. In particular the process is suitable for hydrogenating a composition comprising different $C_1$-$C_3$ oxygenate compounds, such as the product from a thermolytic fragmentation of a sugar composition.

31 Claims, 1 Drawing Sheet

(56) References Cited

FOREIGN PATENT DOCUMENTS

| WO | WO 00/14041 A1 | 3/2000 |
|---|---|---|
| WO | 2005037749 A1 | 4/2005 |
| WO | WO 2005/058788 A1 | 6/2005 |
| WO | 2015055315 A1 | 4/2015 |
| WO | WO 2015/154258 A1 | 10/2015 |
| WO | 2016001136 A1 | 1/2016 |

OTHER PUBLICATIONS

Office Action dated May 9, 2019, by the Taiwanese Patent Office in corresponding Taiwanese Patent Application No. 104121105, and an English Translation of the Office Action. (14 pages).

International Search Report (PCT/ISA/210) dated Mar. 24, 2017, by the European Patent Office as the International Searching Authority for International Application No. PCT/EP2017/050215.

Written Opinion (PCT/ISA/237) dated Mar. 25, 2017, by the European Patent Office as the International Searching Authority for International Application No. PCT/EP2017/050215.

Office Action issued by the U.S. Patent and Trademark Office in the U.S. Appl. No. 16/068,472, dated Mar. 11, 2019, U.S. Patent and Trademark Office, Alexandria, VA. (7 pages).

Office Action (Communication pursuant to Article 94(3) EPC) dated Mar. 2, 2020, by the European Patent Office in corresponding European Application No. 17700115.3-1109. (4 pages).

Office Action dated Mar. 17, 2020 by the Federal Service for Intellectual Property in Russian Patent Application No. 2018128473/04(045 694), (13 pages).

\* cited by examiner

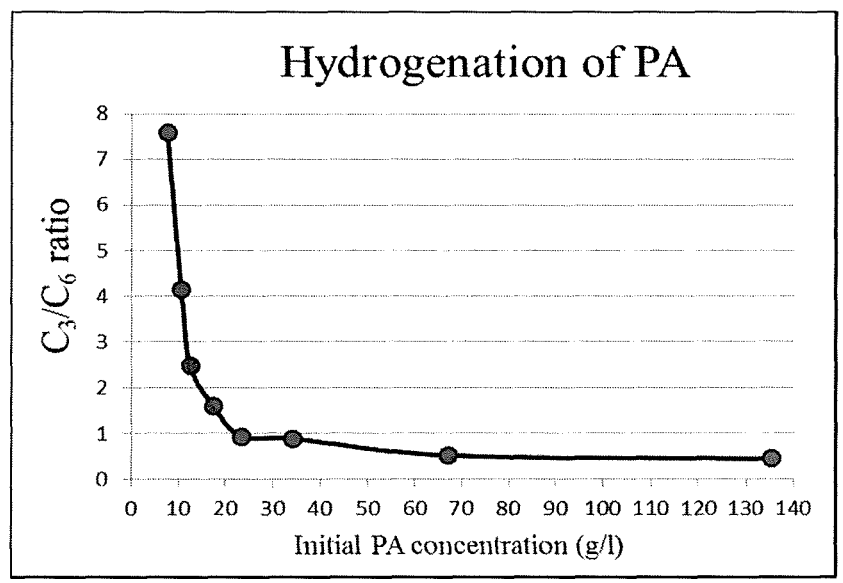

PROCESS FOR THE PREPARATION OF ETHYLENE GLYCOL FROM SUGARS

TECHNICAL FIELD

The invention regards an improved hydrogenation process for catalytic hydrogenation of low molecular weight oxygenate compounds to its hydroxyl counterparts. The method is suitable for converting a $C_1$-$C_3$-oxygenate composition obtained from thermolytic fragmentation of a sugar composition.

BACKGROUND

Ethylene glycol can be prepared by a variety of routes including from sugars, e.g. monosaccharides, disaccharides or syrups, via fermentation and hydrogenolysis processes, or by hydroformylation of formaldehyde.

The fermentation route is a five-step process wherein glucose is fermented to ethanol and carbon dioxide, followed by conversion of ethanol to ethylene, ethylene to ethylene oxide and ethylene oxide to ethylene glycol. One disadvantage of this method is that per mole of glucose fermented, two moles of carbon dioxide are produced together with two moles of ethanol; this has the effect that a theoretical maximum 67% of the carbon present in the glucose can be transformed to ethanol.

The hydrogenolysis route is a two-step process wherein glucose is reduced to sorbitol followed by hydrogenolysis of sorbitol to ethylene glycol, as illustrated by U.S. Pat. No. 6,297,409 B1 and US 2008/0228014 A1. Significant quantities of propylene glycol, compared to ethylene glycol, are formed via the hydrogenolysis process. Additionally, the amount of catalyst used is significant and appears difficult to regenerate in order to reuse. Furthermore, the byproducts formed, in particular butanediols, are difficult to separate from the desired product. In particular, the industrially favorable method of distillation for separation (purification) purposes is extremely difficult to apply as the byproducts have very similar boiling points to the final product, and the desired product may react further, as illustrated in US2014/0039224 A1 and U.S. Pat. No. 5,393,542 B1.

The hydroformylation route is a two-step process wherein glycolaldehyde is prepared from formaldehyde, carbon monoxide and hydrogen, followed by hydrogenation of the glycolaldehyde to ethylene glycol, as illustrated in U.S. Pat. No. 4,496,781 B1. There appears to be several extraction steps present in order to separate formaldehyde from glycolaldehyde and proceed with the hydrogenation reaction.

It is known that sugars may be subjected to thermolytic fragmentation to obtain a fragmentation product composition comprising oxygenate compounds such as glycolaldehyde (U.S. Pat. No. 7,094,932 B2); the crude fragmentation product composition comprises $C_1$-$C_3$ oxygenate compounds, including formaldehyde, glycolaldehyde, glyoxal, pyruvaldehyde and acetol. The main product of this reaction is glycolaldehyde [U.S. Pat. No. 7,094,932 B2]. Water is the solvent of the reaction.

It is also known that pure glycolaldehyde may be hydrogenated to ethylene glycol. U.S. Pat. No. 4,200,765 B1 discloses hydrogenation of glycolaldehyde under severe conditions: at high pressure [3000 psi (ca. 202 bar)], high temperature [150° C.], and with an organic solvent [N-methyl pyrrolidine] in the presence of a palladium on carbon [Pd/C] catalyst for an extended period [5 h]. U.S. Pat. Nos. 4,321,414 B1 and 4,317,946 B1 disclose the hydrogenation of glycolaldehyde with a homogenous ruthenium catalyst and U.S. Pat. No. 4,496,781 B1 discloses a continuous flow hydrogenation at low pressure [500 psi (ca. 35 bar)], high temperature [160° C.] with a ruthenium on carbon catalyst [Ru/C] in ethylene glycol and trace acetonitrile as solvent.

As illustrated, the two steps, pyrolysis of glucose to obtain, inter alia glycolaldehyde, and hydrogenation of pure glycolaldehyde in the liquid phase, appear to be independently feasible. However, in order for the pyrolysis product composition to be hydrogenated, laborious separation processes are employed to remove formaldehyde from the pyrolysis product composition to avoid formaldehyde poisoning of the hydrogenation catalysts [U.S. Pat. No. 5,210,337 B1]. U.S. Pat. No. 5,393,542 B1 discloses an exemplary purification process comprising multiple distillation steps followed by a solvent-induced precipitation to obtain a glycolaldehyde composition free of formaldehyde.

With regard to hydrogenation of glycolaldehyde, although there is the provision of suitable reaction conditions to obtain a high yield in organic solvents, the reaction with water as a solvent appears to be less successful. U.S. Pat. No. 5,393,542 B1 discloses thermal degradation of glycolaldehyde (2-hydroxyacetaldehyde) when subjected to temperatures of 90° C. or higher and where water is the solvent.

EP 0 002 908 B1 discloses the variation in yield (conversion and selectivity) of the hydrogenation of glycolaldehyde with the use of various catalysts in an aqueous solution at 110° C.: Raney Nickel [100% conversion 49.4% selectivity], 10% Pd/C [62% conversion, 61% selectivity] and 10% Pt/C [100% conversion, 73% selectivity]. A problem with catalysts used in liquid water is the strain on the catalyst. However, mild reaction conditions are favorable in order to ensure longevity of the catalyst on an industrial scale.

The choice of catalyst may affect the decomposition of glycolaldehyde when in the presence of the catalyst; U.S. Pat. No. 5,210,337 B1 discloses the problem of glycolaldehyde 'unzipping' to form formaldehyde and consequently poisoning the hydrogenation catalyst. It is also possible that glycolaldehyde may self-condense or condense with another $C_1$-$C_3$ oxygenate compound, also illustrated in U.S. Pat. No. 5,210,337 B1. Accordingly, both the choice of catalyst and the stability of the glycol product may affect the degree of reduction of the glycolaldehyde. E.g. some catalysts may reduce the glycolaldehyde to ethanol or ethane, i.e. over reduce the glycolaldehyde.

Additionally, it is known that an increase in temperature, pressure, concentration of substrate and/or concentration of product as well as the amount and identity of catalyst present may affect the yield (conversion and selectivity) of hydrogenation reactions of glycolaldehyde. Handbook of Heterogeneous Catalytic Hydrogenation for Organic Synthesis, Shigeo Nishimura, ISBN: 978-0-471-39698-7, April 2001.

In summary, the efforts to provide an industrial scale process for hydrogenation of the fragmentation product composition of an industrial scale thermolytic fragmentation of sugars to produce ethylene glycol have shown to be challenging. Formaldehyde formed in the thermolytic fragmentation has shown to poison the hydrogenation catalyst, even at low concentrations. In addition, the reaction conditions have shown to unpredictably affect the selectivity, conversion rate and hydrogenation catalyst lifetime. Finally, formation of unwanted side products may complicate the subsequent purification of the hydrogenation product composition.

Consequently, there is still a need for improving the process of producing ethylene glycol from sugars via thermolytic fragmentation of sugars followed by catalytic hydrogenation of the resulting fragmentation product composition to avoid toxic compositions, obtain higher yields and higher selectivities and reduce the amount of undesirable side products at low costs to make it suitable for industrial scale production of ethylene glycol.

SUMMARY OF INVENTION

The catalytic hydrogenation processes available in the prior art have not been successful in achieving high selectivities for ethylene glycol and even worse for propylene glycol. Also the yields have not been satisfying. Thus the existing processes have not provided methods suitable for industrial scale production of ethylene glycol or propylene glycol. The inventors have found that having the complex composition containing different oxygenates and in addition many other components has made it problematic to conduct a catalytic hydrogenation according to prior art processes.

Process of Producing $C_1$-$C_3$ Hydroxy Compounds from $C_1$-$C_3$ Oxygenate Compounds According to the present invention a process is provided for the preparation of a $C_1$-$C_3$ hydroxy compound, comprising the steps of:
a) Providing an oxygenate feed composition comprising a $C_1$-$C_3$ oxygenate compound in a total concentration of at least 20% by weight of oxygenate feed composition; and
b) Providing a chemical reactor comprising
i. an inlet zone in fluid communication with
ii. a reaction zone comprising a heterogeneous hydrogenation catalyst material in fluid communication with
iii. an outlet zone;
then
c) feeding the oxygenate feed composition of step a) to the reactor inlet zone i) of step b) to obtain an initial total concentration of $C_1$-$C_3$ oxygenate compound of less than 20% by weight of reactor fluid in the reaction zone ii) of step b); and
d) in the reaction zone ii) reacting the $C_1$-$C_3$ oxygenate compound with hydrogen in the presence of the catalyst material to obtain a $C_1$-$C_3$ hydroxy compound; and then
e) Recovering from the outlet zone iii) the hydroxy product composition comprising the $C_1$-$C_3$ hydroxy compound.

The inventors found that lowering the concentration of $C_1$-$C_3$ oxygenate compounds in the reaction zone had surprisingly high impact on the selectivities, in particular for the ethylene glycol and the propylene glycol. In fact, an advantage of the process according to the invention is that the selectivity towards ethylene glycol is at least 80% (moles of ethylene glycol formed per mole $C_2$ oxygenate (glycolaldehyde, glyoxal) converted), preferably at least 85, 88, 90, 91, 92, 93, 94, 95, 96 or 97%, and the selectivity towards propylene glycol is at least 60% (moles of propylene glycol formed per mole $C_3$ oxygenate (pyruvaldehyde, acetol) converted), preferably at least at least 65, 70, 75, 80%, 85, 88, 90, 91, 92, 93, 94, 95, 96 or 97%. A selectivity of at least X % implicitly defines a range wherein the upper limit is a selectivity of 100%. Accordingly, a selectivity of ethylene glycol of at least 80% defines a range of from 80-100%, a selectivity of propylene glycol of at least 60% defines a range of from 60-100% and so forth.

Additional advantages include enabling the use of the oxygenate containing product of thermolytic fragmentation of sugar compositions as feed for the preparation of the corresponding hydroxy compounds at high selectivity and high yield; utilizing non-toxic solvents and cheaper catalysts; reducing byproduct production; enabling purification on an industrial scale; and being successful even in the presence of additional compounds such as formaldehyde. The ability to separate byproducts from the ethylene glycol product enables the ethylene glycol to be used in processes such as polymer production. Polymer production requires substrates to be in a highly pure form. All of these desirable advantages makes the production of in particular ethylene glycol from biomaterials such as sugar more attractive industrially and enable processes to become commercially feasible.

In one aspect, the process according to the present invention has a total concentration of $C_1$-$C_3$ oxygenate compound in the oxygenate feed composition of at least 25% by weight of oxygenate feed composition, such as at least 30% or 35% or 40% or 45% or 50% or 55% or 60% or 65% or 70% or 75% by weight of oxygenate feed composition. In an embodiment of the present invention, the $C_1$-$C_3$ oxygenate compound of the oxygenate feed composition of step a) is a $C_2$-$C_3$ oxygenate compound. In another embodiment of the present invention, the oxygenate feed composition of step a) comprises two or more $C_1$-$C_3$ oxygenate compounds selected from the group consisting of glycolaldehyde, glyoxal, pyruvaldehyde, acetol and formaldehyde. Even with several different oxygenate compounds in the $C_1$-$C_3$ oxygenate feed composition the selectivities obtained are still very high. In a preferred embodiment, the oxygenate feed composition of step a) comprises at least 20% by weight of glycolaldehyde and at least 5% by weight of pyruvaldehyde. Even with such high amounts of glycolaldehyde and in particular of pyruvaldehyde in the $C_1$-$C_3$ oxygenate feed composition the selectivities obtained are still very high.

In an aspect of the present invention, the total concentration by weight of $C_1$-$C_3$ hydroxy compound in the hydroxy product composition is at least 50% by weight of the total concentration of $C_1$-$C_3$ oxygenate compound in the oxygenate feed composition, such as at least 55% or 60% or 65% or 70% or 75% or 80% or 85% or 90% by weight of the total concentration of $C_1$-$C_3$ oxygenate compound in the oxygenate feed composition. Accordingly, the process according to the present invention allows to have a high concentration of $C_1$-$C_3$ oxygenate compound in the oxygenate feed composition, a low concentration of $C_1$-$C_3$ oxygenate compound in the reaction zone and still a high concentration of $C_1$-$C_3$ hydroxy compound in the hydroxy product composition. In an embodiment according to the present invention, the $C_1$-$C_3$ hydroxy compound of the hydroxy product composition of step e) is a $C_2$-$C_3$ hydroxy compound. In another embodiment according to the present invention, the hydroxy product composition of step e) comprises one or more $C_1$-$C_3$ hydroxy compounds selected from the group consisting of methanol, ethylene glycol and propylene glycol.

In an aspect of the present invention the catalyst material of step b) may comprise a metal component selected from the group consisting of ruthenium, ruthenium alloy, rhenium, rhodium, iridium, palladium, platinum, copper and nickel and the support material may be one or more selected from the group consisting of carbon, silica, alumina, titania, and zirconia. Preferred catalyst materials comprises ruthenium on carbon or copper on carbon.

Step d) of the process according to the present invention may be conducted under an initial hydrogen partial pressure of at least 0.5 bar, such as at least 5 bar or at least 40 bar, or between 0.5 and 500 bar or between 0.5 and 200 bar, in particular between 0.5 and 5 bar or between 60 and 140 bar. The reaction of step d) may be conducted under a total pressure of from 0.8-800 bar, such as from 3-500, in particular between 3 and 10 bar or between 40 and 150 bar. The reaction of step d) may be conducted at a temperature in the range of 50-350° C., such as from 50-250° C., 60-120° C., 200-250° C. or from 150-200° C.

The process according to the present invention may be conducted under conditions to provide liquid phase hydrogenation of the oxygenate compound and with a solvent present in the reaction zone of step d). The inventors have observed challenges in obtaining good selectivities towards ethylene glycol and propylene glycol in catalytic liquid phase hydrogenation of glycolaldehyde and pyruvaldehyde.

The reaction conditions of the process according to the present invention may be chosen so that the $C_1$-$C_3$ oxygenate compounds and the $C_1$-$C_3$ hydroxy compounds are essentially in the liquid phase or in the gas phase during the hydrogenation reaction.

When the hydrogenation is a liquid phase hydrogenation, the hydrogenation is preferably conducted at a temperature in the range of from 60-120° C. and a hydrogen partial pressure in the range of from 60-140 bar. When the hydrogenation is a liquid phase hydrogenation, the partial pressure of hydrogen is the partial pressure in the gas phase above, or interspersed with, the hydrogenation fluid, which is proportional to the concentration of hydrogen in the liquid phase.

When the hydrogenation is a gas phase hydrogenation, the hydrogenation is preferably conducted at a temperature in the range of from 200-250° C. and a hydrogen partial pressure in the range of from 0.5 and 5 bar.

According to an embodiment of the present invention, the solvent is selected from the group consisting of water, methanol, ethanol, ethylene glycol and propylene glycol; or mixtures thereof.

The process according to the present invention is even more advantageous when performed under continuous conditions. Preferably the chemical reactor comprises an inlet and an outlet to accommodate continuous operation of the process.

The hydrogenation may be conducted in a plug flow, or primarily plug flow, type reactor such as a packed bed reactor, a fixed bed reactor, a trickle bed reactor, a fluid bed reactor or a slurry phase reactor. In such reactors a fraction of the hydroxy product composition recovered in step e) may advantageously be transferred to the reaction zone ii) of step b). This recirculation of product to the reactor is a highly advantageous way of lowering the oxygenate concentration in the reaction zone. Not only is the oxygenate concentration lowered, but the glycols of the product stream have a further stabilizing effect on the oxygenates. On an industrial scale it is highly advantageous to use the product as a solvent/diluent in the reaction zone, since there is no need to remove the solvent after the hydrogenation reaction.

It may also be conducted in a stirred tank type reactor, such as a CSTR or a Berty reactor. In this case the backmixing is so pronounced that upon entering the reaction zone, the oxygenate feed composition is mixed with high amounts of product thus lowering the concentration of oxygenates almost instantly.

As the hydrogenation reaction is highly exothermic, it is desirable to choose reactors having means to control the temperature rise in the hydrogenation reactors. Some reactors suitable for heat removal could be, but is not limited to, multitubular reactors, reactors having cooling between the different catalyst layers (interbed cooling) or recycle reactors.

For liquid phase hydrogenation, an industrially promising reactor approach could be a so called trickle bed reactor, where liquid flows downward over the catalyst bed, and gas is added in either co-current or counter-current flow. A recycle can be used to control the temperature increase in the reactor. In addition, the recycle will serve to dilute the reactants.

Another promising reactor configuration is the slurry-bed reactor (ebullating bed). In this reactor, hydrogen is fed from the bottom and 'bubbles' through the substrate liquid containing the suspended catalyst. A submerged cooling coil in the slurry bed can be used to control the temperature. Due to in-bed temperature control and higher degree of backmixing, a smaller (or no) recycle is required in the slurry-bed compared to the trickle bed reactor.

Comparing the chemical reactor performance of the trickle bed and slurry reactor, the first will provide a higher degree of plug flow and the second reactor a higher degree of isothermal conditions.

The hydrogenation product composition of d) may be subjected to a purification step, such as distillation, filtration, adsorption and/or ion exchange to recover the hydroxyl compounds. Unreacted hydrogen recovered in the purification step, may be recycled to the reaction zone ii) of step b).

The oxygenate feed composition of step a) may be derived from a thermolytic fragmentation of a sugar composition.

Process of Producing $C_1$-$C_3$ Hydroxy Compounds from Sugar Compositions

According to the present invention, a process for the preparation of a $C_1$-$C_3$ hydroxy compound from a sugar composition is provided, comprising the steps of:
  i. Providing a feedstock solution of a sugar composition;
  ii. Exposing the feedstock of a) to thermolytic fragmentation to produce a fragmentation product composition comprising a $C_1$-$C_3$ oxygenate compound; and
  iii. Optionally conditioning the fragmentation product composition; and then
  iv. Subjecting the fragmentation product composition of step ii) or iii) to the hydrogenation process according to the present invention, wherein the fragmentation product composition is the oxygenate feed composition of step a) of the hydrogenation process according to the present invention.

The optional conditioning of step iii) may comprise a distillation, filtration, adsorption and/or ion exchange to remove impurities prior to the hydrogenation.

The sugar composition of the feedstock solution for thermolytic fragmentation may be selected from one or more of the monosaccharides fructose, xylose, glucose, mannose, galactose arabinose; the disaccharides sucrose, lactose, maltose or from syrups such as corn syrup, cane sugar syrup or whey. The feedstock solution of step i) is generally a solution of a sugar in a solvent comprising from 20-95 wt. %, such as from 50-90 wt % of sugar. The solvent may comprise one or more of the compounds selected from the group consisting of water, methanol, ethanol, ethylene glycol and propylene glycol. It is an advantage in the fragmentation step to use solvents comprising alcohols, since the evaporation energy is lower than water.

$C_1$-$C_3$ hydroxy products such as ethylene glycol and propylene glycol obtained from bio materials, such as sugars, will have a significantly higher content of $^{14}C$ than the same products obtained from petrochemical sources.

Accordingly, a product is provided according to the present invention, which is obtainable by the process for the preparation of a $C_1$-$C_3$ hydroxy compound from a sugar composition described above. Such a product is characteristic by having a $^{14}C$ content above 0.5 parts per trillion of the total carbon content. The $C_1$-$C_3$ hydroxy compound may be ethylene glycol and at least 70% of the initial carbon may be recovered in the form of ethylene glycol or propylene glycol. According to an embodiment of the present invention, a product is provided which is obtainable by the process according to the present invention, which is characterized in that the product has a $^{14}C$ content above 0.5 parts per trillion (weight by weight) of the total carbon content; and in that at least 70% of the initial carbon is recovered in the form of ethylene glycol or propylene glycol in the hydrogenation product composition.

The $C_1$-$C_3$ hydroxy compound prepared according to the invention, such as ethylene glycol or propylene glycol, may be used for the preparation of a polymer, such as polyethylene terephthalate, polyester resins, fibres or films. The polymer will have a $^{14}C$ content reflecting the fraction of monomers which have been obtained from biomaterials.

The $C_1$-$C_3$ hydroxy compound prepared according to the invention, such as ethylene glycol or propylene glycol, may also be used as a de-icing agent, coolant, anti-freeze agent or solvent.

In and embodiment according to the present invention a system for continuously performing the process disclosed herein is provided, said system comprising a hydrogenation unit, such as a multi-tubular reactor, having an inlet and an outlet and a hydrogenation catalyst as defined herein, and a thermolytic fragmentation unit having an inlet and outlet, wherein the outlet of said thermolytic fragmentation unit is fluidly connected to the inlet of said hydrogenation unit. In an embodiment, the outlet of said thermolytic fragmentation unit is directly, fluidly connected to the inlet of said hydrogenation unit. The fragmentation unit comprises a fragmentation reactor comprising a suitable inlet for the feedstock and an outlet for a fragmentation product composition (stream). The hydrogenation unit comprises a chemical reactor comprising suitable inlets for the oxygenate feed composition and hydrogen and outlets for a hydroxy product composition (stream) and excess hydrogen.

In an embodiment according to the present invention, the outlet of the fragmentation unit is directly, fluidly connected with the inlet of the hydrogenation unit by means of piping equipment suitable for conveying high temperature gases and liquids. "Directly" is intended to refer to a transfer from the fragmentation unit to the hydrogenation unit which is not interrupted by significant delays nor by purification. However, it may be condensed to accommodate liquid hydrogenation. An advantage of the direct transfer of fragmentation product to hydrogenation unit is that the heat remaining in the fragmentation product may be retained and if the hydrogenation is a gas phase hydrogenation a step of evaporating the feed may be dispensed with, since it is already in the gas phase.

In another embodiment according to the present invention, the system further has a hydrogen recycle from the outlet of the hydrogenation unit to the inlet or the hydrogen inlet of the hydrogenation unit. Accordingly, excess hydrogen may be recycled to the hydrogenation unit thus improving cost efficiency. The recycle may be connected with the hydrogen inlet or may be recycled directly into the chemical reactor.

BRIEF DESCRIPTION OF THE DRAWINGS

FIG. 1: $C_3$/$C_6$ ratio plotted as a function of initial pyruvaldehyde concentration (40 mg of Ru/C added as catalyst). $C_3$ comprises acetol and propylene glycol and $C_6$ comprises all $C_6$ byproducts formed by aldol condensation of pyruvaldehyde.

DEFINITIONS

The term "oxygenate feed composition" is meant to refer to the oxygenate containing fluid passing through the inlet of the reactor used for conducting the hydrogenation. When the oxygenate composition is obtained from a thermolytic fragmentation of a sugar composition, it may in addition to the $C_1$-$C_3$ oxygenate compounds, contain other compounds e.g. organic acids such as acetic acid, formic acid, glycolic acid and/or lactic acid; furans such as furfural and/or 5-(hydroxymethyl)furfural; and solvents such as water.

In the present context, the term "$C_1$-$C_3$ oxygenate compound" is meant to refer to an organic compound containing between 1 and 3 carbon atoms and at least one carbonyl bond (ketone or aldehyde).

The term "oxygenate feed composition comprising a $C_1$-$C_3$ oxygenate compound" is meant to refer to an oxygenate feed composition comprising one or more $C_1$-$C_3$ oxygenate compounds. It may also comprise minor amounts of other organic compounds.

In the present context, a "gas phase hydrogenation" is meant to refer to a hydrogenation wherein the substrate (here the $C_1$-$C_3$ oxygenate compound) is essentially in a gaseous form in the reaction zone of the catalytic material. For example, at least 80 wt. %, such as at least 90, 92, 94 or 96 wt. %, is in the gaseous form. Accordingly, this means that 80-100 wt. %, such as 90-100, 92-100, 94-100 or 96-100 wt %, is in the gaseous form.

In the present context, a "liquid phase hydrogenation" is meant to refer to a hydrogenation wherein the substrate (here the $C_1$-$C_3$ oxygenate compound) is essentially in liquid solution in the reaction zone of the catalytic material. For example, at least 80 wt. %, such as at least 90, 92, 94 or 96 wt. %, is in the liquid form. Accordingly, this means that 80-100 wt. %, such as 90-100, 92-100, 94-100 or 96-100 wt. %, is in the liquid form.

In the present context, a "reaction zone" is meant to refer to the area around the catalyst wherein the oxygenate feed composition is brought into contact with the hydrogenation catalyst. In certain embodiments the reaction zone may be defined by the walls of the chemical reactor. In a continuous reactor, the reaction zone may be defined by the reactor walls and the inlet and the outlet. In liquid hydrogenation the reaction zone is the liquid reactor fluid. In gaseous hydrogenation the reaction zone is defined by the reactor walls and if inlet and outlet is present, by the end of the inlet and the beginning of the outlet.

The term "hydrogenation product composition" is meant to refer to the hydroxy containing fluid resulting from the hydrogenation reaction. When the hydrogenation product composition is obtained from hydrogenating the fragmentation product of a thermolytic fragmentation of a sugar composition, it may in addition to the $C_1$-$C_3$ hydroxy compounds, contain other compounds e.g. organic acids such as acetic acid, formic acid, glycolic acid and/or lactic acid; furans such as furfural and/or 5-(hydroxymethyl)furfural; and solvents such as water.

Concentrations given in percentages are to be understood as weight % (i.e. weight of x per total weight), where nothing else is stated.

In the present context, the term "$C_1$-$C_3$ hydroxy compound" is meant to refer to an organic compound which contains between 1 and 3 carbon atoms and at least one hydroxyl group (alcohol) and which may be produced by hydrogenation of a $C_1$-$C_3$ oxygenate compound.

The term "hydrogenation product composition comprising a $C_1$-$C_3$ hydroxy compound" is meant to refer a hydrogenation product composition comprising one or more $C_1$-$C_3$ hydroxy compounds.

The term "catalytic material" is to be understood as any material which is catalytically active. This is also the meaning of the term "catalyst". All terms may be used interchangeably.

The terms "Cu on carbon" and "Cu/C" are meant to refer to a catalytically active material having a support of carbon (such as activated carbon/carbon nanotubes/graphene/fullerenes) with copper particles deposited on the support. As the skilled person will know, it is mainly the surface of the Cu particles which provide the catalytic activity. Accordingly, a large Cu particle surface area is desirable.

The term "Recovering" is meant to refer either to collecting the hydrogenation product composition or to directing the hydrogenation product composition to a subsequent step, such as to a purification unit.

The term "yield" is in the present context meant to refer to the molar fraction of $C_1$-$C_3$ oxygenate compound which is converted into its corresponding $C_1$-$C_3$ hydroxy compound (i.e. $C_1$ to $C_1$; $C_2$ to $C_2$; and $C_3$ to $C_3$).

The term "conversion" is in the present context meant to refer to the molar fraction of $C_1$-$C_3$ oxygenate compound which has reacted during the hydrogenation process to form either the desired $C_1$-$C_3$ hydroxy compound or other products.

The term "selectivity" is meant to refer to the molar fraction of desired product formed per substrate converted. In the present context the substrate for a $C_1$ hydroxy compound is only considered to be the $C_1$ oxygenate compounds present in the oxygenate feed composition; for a $C_2$ hydroxy compound the substrate is only considered to be the $C_2$ oxygenate compounds present in the oxygenate feed composition; and for a $C_3$ hydroxy compound the substrate is only considered to be the $C_3$ oxygenate compounds present in the oxygenate feed composition. The selectivity may be calculated as yield divided by conversion.

The term "initial" (hydrogen partial pressure/oxygenate molar fraction/oxygenate concentration etc.) is meant to refer to the partial pressure or molar fraction at the time when it first meets the catalytic material.

The term "continuous conditions" is meant to refer to truly continuous conditions (such as in a fluid bed reactor or packed bed reactor, optionally with recycle of the hydrogenation product composition to the feed stream or to the reactor inlet) but it is also meant to refer to semi-continuous conditions such as repeatedly feeding small portions of the oxygenate feed composition to the reactor fluid and repeatedly collecting small portions of the hydroxy product composition from the reactor outlet.

The "reactor fluid" is meant to refer to the fluid present in the reaction zone, including both unreacted oxygenate compounds, the hydroxy compounds formed and any solvent or diluent present.

EXAMPLE

Example 1: Effect of Initial $C_1$-$C_3$ Oxygenate Concentration

The experiment was performed in an autoclave. 3.1 g $C_1$-$C_3$ oxygenate feed composition was fed to the autoclave. The concentration of $C_1$-$C_3$ oxygenates in the $C_1$-$C_3$ oxygenate feed composition varied according to Table 1 below. The $C_1$ oxygenates present in the $C_1$-$C_3$ oxygenate feed composition were mainly formaldehyde (FA). The $C_2$ oxygenates present in the $C_1$-$C_3$ oxygenate feed composition were mainly glycolaldehyde (GA) and glyoxal. The $C_3$ oxygenates present in the $C_1$-$C_3$ oxygenate feed composition were mainly pyruvaldehyde (PA) and acetol. Accordingly the initial glycolaldehyde (GA) concentration ranged from 16 g/l to 264 g/l. The $C_1$-$C_3$ oxygenate feed composition was hydrogenated for 16 hours at 80° C. and 90 bar $H_2$ with 0.040 g of 5% Ru/C catalyst. The catalyst amount was kept constant in all experiments meaning that the relative amount of catalyst compared to substrate increased with decreasing oxygenate concentration. After hydrogenation, the hydrogenation product composition was recovered and the content of ethylene glycol (EG) and propylene glycol (PG) was determined using standard methods. The yield of EG was calculated as moles of EG formed per mole of glycolaldehyde and glyoxal in the feed composition. The yield of PG was calculated as moles of PG formed per mole of pyruvaldehyde and acetol in the feed composition. Table 1 presents an overview of the results. Full conversion of GA was obtained at GA concentrations up to 129 g/l (entry 1-4). From these experiments it can be seen that the yield of ethylene glycol (EG) decreased with increasing oxygenate concentration. The higher GA concentrations of 196 g/l and 264 g/l did not reach full conversion after 16 hours (entry 5 and 6), the drop in EG selectivity was seen to continue to 82% and 74%, respectively. The trend observed with respect to EG yield was similar for the PG yield.

TABLE 1

Hydrogenation of $C_1$-$C_3$ oxygenate feed compositions of different oxygenate concentrations

| Entry | $C_3$ in feed | $C_2$ in feed | $C_1$ in feed | $C_2$ conversion | EG yield | EG selectivity | PG yield |
|---|---|---|---|---|---|---|---|
| 1 | 2.4 g/l | 16 g/l | 1.4 g/l | 100% | 96% | 96% | 71% |
| 2 | 4.7 g/l | 31 g/l | 2.7 g/l | 100% | 95% | 95% | 68% |
| 3 | 9 g/l | 62 g/l | 5.4 g/l | 100% | 93% | 93% | 61% |
| 4 | 20 g/l | 129 g/l | 11 g/l | 100% | 85% | 85% | 50% |
| 5 | 29 g/l | 196 g/l | 17 g/l | 96% | 78% | 82% | 45% |
| 6 | 40 g/l | 264 g/l | 23 g/l | 44% | 33% | 74% | n.a. |

Example 2: Continuous Process

A continuously stirred tank reactor (CSTR) setup was used to perform the hydrogenation of an oxygenate mixture. The CSTR consisted of a 500 ml autoclave, with the possibility of feeding liquid and gas to the reactor, as well as withdrawing reaction liquid and gas from the reactor. The hydrogenation was performed by loading 20 g of a 5 wt. % Ru/C catalyst in a Robinson-Mahoney catalyst basket, which was mounted in the autoclave. The autoclave was then filled with 300 ml of water, sealed, and flushed with nitrogen. The reactor was pressurized to 80 bar, using hydrogen, and the temperature increased to 90° C. Hydrogen was supplied to the reactor at a rate of 80 Nml/min, while gas was withdrawn from the reactor at a rate sufficient to keep the pressure constant. An oxygenate feed with the composition given in Table 2 was fed to the reactor at a rate of 0.1 g/min, while liquid product was withdrawn at the same rate to give a constant amount of reaction liquid in the reactor. Due to the vigorous stirring of the reactor, the feed being supplied to the reactor was almost immediately completely mixed with the liquid in the reactor upon entering the reactor, essentially diluting the feed with the product composition. As the reactor, under these conditions, operate at high conversion (i.e. >95%), this means that the substrate concentration in the reaction zone is constantly low. When steady state had been achieved, the content of ethylene glycol (EG) and propylene glycol (PG) in the recovered hydrogenation product composition was determined using standard methods. A yield of EG of 85% was achieved. A yield of PG of 70% was achieved.

TABLE 2

Concentration of oxygenates in feed.

| Compound | Concentration [g/L] |
|---|---|
| Glycolaldehyde | 244 |
| Formaldehyde | 38 |
| Pyruvaldehyde | 22 |
| Glyoxal | 16 |
| Acetol | 14 |

The invention claimed is:

1. A process for the preparation of a $C_1$-$C_3$ hydroxy compound, comprising the steps of:
   a) providing an oxygenate feed composition comprising a $C_1$-$C_3$ oxygenate compound in a total concentration of at least 20% by weight of oxygenate feed composition; and
   b) providing a chemical reactor comprising
      i. an inlet zone in fluid communication with
      ii. a reaction zone comprising a heterogeneous hydrogenation catalyst material in fluid communication with
      iii. an outlet zone;
   then
   c) feeding the oxygenate feed composition of step a) to the reactor inlet zone i) of step b) to obtain an initial total concentration of $C_1$-$C_3$ oxygenate compound of less than 20% by weight of reactor fluid in the reaction zone ii) of step b), wherein change in the total concentration of $C_1$-$C_3$ oxygenate compound from greater than 20% by weight to less than 20% by weight is due to dilution by the reactor fluid; and
   d) in the reaction zone ii) reacting the $C_1$-$C_3$-oxygenate compound with hydrogen in the presence of the catalyst material to obtain a $C_1$-$C_3$ hydroxy compound; and then
   e) recovering from the outlet zone iii) the hydroxy product composition comprising the $C_1$-$C_3$ hydroxy compound,
   wherein the oxygenate feed composition of step a) comprises two or more $C_1$-$C_3$ oxygenate compounds selected from the group consisting of glycolaldehyde, glyoxal, pyruvaldehyde, acetol and formaldehyde.

2. The process according to claim 1, wherein the total concentration of $C_1$-$C_3$ oxygenate compound in the oxygenate feed composition is at least 25% by weight of oxygenate feed composition.

3. The process according to claim 1, wherein the oxygenate feed composition of step a) comprises at least 20% by weight of glycolaldehyde and at least 5% by weight of pyruvaldehyde.

4. The process according to claim 1, wherein the total concentration by weight of $C_1$-$C_3$ hydroxy compound in the hydroxy product composition is at least 50% by weight of the total concentration $C_1$-$C_3$ oxygenate compound in the oxygenate feed composition.

5. The process according to claim 1, wherein the selectivity of ethylene glycol (mol/mol $C_2$) is at least 80%.

6. A process for the preparation of a C1-C3 hydroxy compound, comprising the steps of:
   a) providing an oxygenate feed composition comprising a C1-C3 oxygenate compound in a total concentration of at least 20% by weight of oxygenate feed composition; and
   b) providing a chemical reactor, wherein the chemical reactor is a continuously stirred tank reactor, comprising
      i. an inlet zone in fluid communication with
      ii. a reaction zone comprising a heterogeneous hydrogenation catalyst material in fluid communication with
      iii. an outlet zone;
   then
   c) feeding the oxygenate feed composition of step a) to the reactor inlet zone i) of step b) to obtain an initial total concentration of C1-C3 oxygenate compound of less than 20% by weight of reactor fluid in the reaction zone ii) of step b); and
   d) in the reaction zone ii) reacting the C1-C3-oxygenate compound with hydrogen in the presence of the catalyst material to obtain a C1-C3 hydroxy compound; and then
   e) recovering from the outlet zone iii) the hydroxy product composition comprising the C1-C3 hydroxy compound,
   wherein the oxygenate feed composition of step a) comprises two or more C1-C3 oxygenate compounds selected from the group consisting of glycolaldehyde, glyoxal, pyruvaldehyde, acetol and formaldehyde, and
   wherein, the selectivity of propylene glycol (mol/mol $C_3$) is at least 60%.

7. The process according to claim 1, wherein the hydroxy product composition of step e) comprises one or more $C_1$-$C_3$ hydroxy compounds selected from the group consisting of methanol, ethylene glycol and propylene glycol.

8. The process according to claim 1, wherein the $C_1$-$C_3$ oxygenate compound is a $C_2$-$C_3$ oxygenate compound.

9. The process according to claim 1, wherein the $C_1$-$C_3$ hydroxy compound is a $C_2$-$C_3$ hydroxy compound.

10. The process according to claim 1, wherein the catalyst material of step b) comprises a metal component selected from the group consisting of ruthenium, ruthenium alloy, rhenium, rhodium, iridium, palladium, platinum, copper and nickel.

11. The process according to claim 1, wherein the catalyst material of step b) comprises a support material.

12. The process according to claim 1, wherein the catalyst material of step b) comprises ruthenium on carbon or copper on carbon.

13. The process according to claim 1, wherein the catalytic reaction of step d) is conducted under an initial hydrogen partial pressure of at least 0.5 bar.

14. The process according to claim 1, wherein the reaction of step d) is conducted at a temperature in the range of from 50-350° C.

15. The process according to claim 1, wherein the reaction of step d) is conducted at a temperature in the range of from 200-250° C. and a hydrogen partial pressure in the range of from 0.5 to 5 bar.

16. The process according to claim 1, wherein the reaction of step d) is conducted at a temperature in the range of from 60-120° C. and a hydrogen partial pressure in the range of from 60 to 140 bar.

17. The process according to claim 1, wherein step d) is conducted under conditions to provide liquid phase hydrogenation of the oxygenate compound and a solvent is present in the reaction zone of step d).

18. The process according to claim 17, wherein the solvent comprises one or more of the compounds selected from the group consisting of water, methanol, ethanol, ethylene glycol and propylene glycol.

19. The process according to claim 1, wherein the process is performed under continuous conditions.

20. The process according to claim 1, wherein the reactor of step c) is a plug flow reactor.

21. The process according to claim 1, wherein a fraction of the hydroxy product composition recovered in step e) is transferred to the reaction zone ii) of step b).

22. The process according to claim 1, wherein the reactor of step c) is a stirred tank reactor.

23. The process according to claim 1, wherein the hydrogenation product composition of step e) is subjected to a purification step to recover the $C_1$-$C_3$ hydroxy compound.

24. The process according to claim 23, wherein unreacted hydrogen recovered in the purification step, is recycled to the reaction zone ii) of step b).

25. A process for the preparation of a $C_1$-$C_3$ hydroxy compound, comprising the steps of:
   i. providing a feedstock solution of a sugar composition;
   ii. exposing the feedstock of a) to thermolytic fragmentation to produce a fragmentation product composition comprising a $C_1$-$C_3$ oxygenate compound; and
   iii. optionally conditioning the fragmentation product composition; and then
   iv. subjecting the fragmentation product composition of step ii) or iii) to the process according to claim 1, wherein the fragmentation product composition is the oxygenate feed composition of step a).

26. The process according to claim 25, wherein the sugar composition is selected from one or more of the monosaccharides fructose, xylose, glucose, mannose, galactose, arabinose; and/or the disaccharides sucrose, lactose, maltose.

27. The process according to claim 25, wherein the feedstock solution of step i) is a solution of a sugar in a solvent comprising from 20-95 wt. % of sugar.

28. The process according to claim 25, wherein the solvent comprises one or more of the compounds selected from the group consisting of water, methanol, ethanol, ethylene glycol and propylene glycol.

29. The process according to claim 1, wherein the oxygenate feed of step a) comprises a $C_1$-$C_3$ oxygenate compound in a total concentration of at least 50% by weight of oxygenate feed composition.

30. The process according to claim 29, wherein a change in the total concentration of $C_1$-$C_3$ oxygenate compound from greater than 50% by weight to less than 20% by weight is due to dilution by the reactor fluid.

31. The process according to claim 1, wherein the chemical reactor is a continuously stirred tank reactor.

* * * * *